(12) United States Patent
Malyugin et al.

(10) Patent No.: US 11,602,456 B2
(45) Date of Patent: *Mar. 14, 2023

(54) RING USED IN A SMALL PUPIL PHACOEMULSIFICATION PROCEDURE

(71) Applicants: Boris Malyugin, Moscow (RU); MicroSurgical Technology, Inc., Redmond, WA (US)

(72) Inventors: Boris Malyugin, Moscow (RU); Vaclav Dusek, Bellevue, WA (US); Lawrence Laks, Bellevue, WA (US)

(73) Assignee: MicroSurgical Technology, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/745,668

(22) Filed: Jan. 17, 2020

(65) Prior Publication Data

US 2020/0315845 A1   Oct. 8, 2020

Related U.S. Application Data

(63) Continuation of application No. 13/661,982, filed on Oct. 26, 2012, now Pat. No. 10,537,470, which is a
(Continued)

(51) Int. Cl.
*A61F 9/007* (2006.01)
*A61B 17/02* (2006.01)
*A61F 9/00* (2006.01)

(52) U.S. Cl.
CPC ...... *A61F 9/00736* (2013.01); *A61B 17/0231* (2013.01); *A61F 9/0017* (2013.01)

(58) Field of Classification Search
CPC ............... A61F 9/00736; A61F 9/0017; A61B 17/0231
See application file for complete search history.

(56) References Cited

U.S. PATENT DOCUMENTS

| 1,506,186 A | 8/1924 | Owen et al. |
| 2,761,457 A | 9/1956 | Wood |

(Continued)

FOREIGN PATENT DOCUMENTS

| CA | 2512606 A1 | 8/2004 |
| DE | 93 20 127 U1 | 4/1994 |

(Continued)

OTHER PUBLICATIONS

Specification of U.S. Appl. No. 60/918,405. (Year: 2007).*
(Continued)

*Primary Examiner* — Paul B Prebilic
(74) *Attorney, Agent, or Firm* — Hamilton, Brook, Smith & Reynolds, P.C.

(57) ABSTRACT

A method of implanting a continuous iris-expanding ring in an eye involves ejecting the continuous iris-expanding ring from a distal end of a cannula toward an iris of the eye, securing a distal portion of the continuous iris-expanding ring device ring to the iris of the eye, and securing a proximal portion of the continuous iris-expanding ring to the iris of the eye. The continuous iris-expanding ring is in a collapsed configuration in the cannula prior to being ejected and in an expanded configuration when the proximal portion and the distal portion of the continuous iris-expanding ring are secured to the iris of the eye and extend across the pupil.

9 Claims, 4 Drawing Sheets

Related U.S. Application Data continuation of application No. 12/074,742, filed on Mar. 5, 2008, now Pat. No. 8,323,296.

(60) Provisional application No. 60/918,405, filed on Mar. 15, 2007.

(56) References Cited

U.S. PATENT DOCUMENTS

| | | | |
|---|---|---|---|
| 3,975,779 A | 8/1976 | Richards et al. | |
| 4,037,589 A | 7/1977 | McReynolds | |
| 4,177,802 A | 12/1979 | Ogami | |
| 4,203,168 A | 5/1980 | Rainin et al. | |
| 4,321,916 A | 3/1982 | McKee | |
| 4,387,706 A | 6/1983 | Glass | |
| 4,412,532 A | 11/1983 | Anthony | |
| 4,428,746 A | 1/1984 | Mendez | |
| 4,446,582 A | 5/1984 | Hanna | |
| 4,782,820 A | 11/1988 | Woods | |
| 4,991,567 A | 2/1991 | McCuen et al. | |
| 5,163,419 A | 11/1992 | Goldman | |
| 5,267,553 A | 12/1993 | Graether | |
| 5,290,292 A | 3/1994 | Householder | |
| 5,299,564 A * | 4/1994 | Sabatino | A61F 9/007 606/198 |
| 5,318,011 A | 6/1994 | Federman et al. | |
| 5,322,054 A | 6/1994 | Graether | |
| 5,334,217 A | 8/1994 | Das | |
| 5,374,272 A | 12/1994 | Arpa et al. | |
| 5,427,088 A | 6/1995 | Graether | |
| 5,441,045 A | 8/1995 | Federman et al. | |
| 5,456,274 A * | 10/1995 | Selbee | A45D 8/00 132/275 |
| 5,489,295 A * | 2/1996 | Piplani | A61F 2/958 623/1.34 |
| 5,634,884 A * | 6/1997 | Graether | A61F 2/1662 600/210 |
| 5,693,085 A * | 12/1997 | Buirge | A61F 2/0022 623/1.13 |
| 5,951,565 A * | 9/1999 | Freeman | A61F 2/15 623/6.11 |
| 6,068,643 A * | 5/2000 | Milverton | A61B 17/0231 606/107 |
| 6,200,336 B1 * | 3/2001 | Pavcnik | A61F 2/2475 623/1.13 |
| 6,231,583 B1 | 5/2001 | Lee | |
| 6,332,866 B1 * | 12/2001 | Grieshaber | A61B 17/0231 600/210 |
| 6,497,724 B1 * | 12/2002 | Stevens | A61F 2/86 623/1.22 |
| 6,620,098 B1 * | 9/2003 | Milverton | A61B 17/0231 600/236 |
| 6,814,748 B1 * | 11/2004 | Baker | A61F 2/07 623/1.36 |
| 7,305,996 B2 * | 12/2007 | Kraft | A45D 8/34 132/273 |
| 7,412,993 B2 * | 8/2008 | Tzeng | A61F 2/885 623/1.22 |
| 7,985,180 B2 | 7/2011 | Brown | |
| 7,985,190 B2 * | 7/2011 | Gruber | A61H 23/0245 601/2 |
| 8,257,256 B1 * | 9/2012 | Krolman | A61B 17/0231 600/236 |
| 8,323,296 B2 * | 12/2012 | Malyugin | A61B 17/0231 606/4 |
| 8,376,743 B1 * | 2/2013 | Bukhary | A61C 5/90 600/209 |
| 8,439,833 B2 | 5/2013 | Christensen et al. | |
| 8,439,933 B2 * | 5/2013 | Akahoshi | A61F 9/00745 606/107 |
| 8,496,583 B1 * | 7/2013 | Reynard | A61B 17/0231 600/235 |
| 8,900,136 B2 * | 12/2014 | Cote | A61B 17/0293 600/236 |
| 9,089,397 B2 | 7/2015 | Clarke | |
| D735,857 S * | 8/2015 | Dykes | D24/150 |
| 9,504,459 B1 * | 11/2016 | Nallakrishnan | A61B 17/0231 |
| 9,763,653 B2 * | 9/2017 | Malyugin | A61B 1/32 |
| 9,918,710 B2 * | 3/2018 | Malyugin | A61B 1/32 |
| 9,974,688 B2 * | 5/2018 | Malyugin | A61B 17/0231 |
| 9,980,852 B2 * | 5/2018 | Malyugin | A61F 9/00736 |
| 10,080,558 B2 * | 9/2018 | Bhattacharjee | A61B 17/0293 |
| 10,357,235 B2 * | 7/2019 | Dykes | A61F 9/0017 |
| 10,517,582 B2 * | 12/2019 | Malyugin | A61B 1/32 |
| 10,537,470 B2 * | 1/2020 | Malyugin | A61F 9/00736 |
| 10,537,473 B2 * | 1/2020 | Malyugin | A61B 17/0231 |
| 11,219,438 B2 * | 1/2022 | Malyugin | A61B 17/0231 |
| 2002/0004676 A1 * | 1/2002 | Wallace | A61B 17/1214 623/1.12 |
| 2002/0120277 A1 * | 8/2002 | Hauschild | A61F 2/95 606/108 |
| 2003/0092970 A1 * | 5/2003 | Lee | A61B 17/0231 600/236 |
| 2005/0192606 A1 * | 9/2005 | Paul, Jr. | A61B 17/320725 606/167 |
| 2007/0239141 A1 * | 10/2007 | Hartley | A61B 17/221 606/1 |
| 2008/0108879 A1 * | 5/2008 | Brown | A61B 17/0231 600/236 |
| 2008/0243139 A1 * | 10/2008 | Dusek | A61B 17/0231 606/107 |
| 2008/0262592 A1 * | 10/2008 | Jordan | A61F 2/95 623/1.11 |
| 2008/0269888 A1 * | 10/2008 | Malyugin | A61B 17/0231 623/6.38 |
| 2008/0275461 A1 * | 11/2008 | Nallakrishnan | A61F 9/007 606/107 |
| 2009/0259260 A1 * | 10/2009 | Bentley | A61B 17/0487 606/228 |
| 2010/0274257 A1 * | 10/2010 | Neusidl | A61F 9/0017 606/107 |
| 2012/0136322 A1 * | 5/2012 | Alster | A61K 31/5575 604/290 |
| 2012/0289786 A1 * | 11/2012 | Dusek | A61B 17/0231 600/236 |
| 2013/0053860 A1 * | 2/2013 | Malyugin | A61B 17/0231 606/107 |
| 2013/0096386 A1 * | 4/2013 | Christensen | A61B 17/0231 600/206 |
| 2013/0131458 A1 * | 5/2013 | Malyugin | A61B 1/32 600/236 |
| 2013/0267988 A1 * | 10/2013 | Sussman | A61B 17/0231 606/198 |
| 2013/0331939 A1 | 12/2013 | Stevens | |
| 2014/0221759 A1 * | 8/2014 | Mackool | A61B 17/0231 600/209 |
| 2014/0378773 A1 * | 12/2014 | Dykes | A61F 9/0017 600/208 |
| 2015/0164658 A1 * | 6/2015 | Jones | A61F 2/4637 606/99 |
| 2015/0164685 A1 | 6/2015 | Bhattachaijee | |
| 2015/0265269 A1 * | 9/2015 | Malyugin | A61B 17/0231 600/236 |
| 2017/0265851 A1 * | 9/2017 | Kahook | A61B 3/00 |
| 2017/0312126 A1 * | 11/2017 | Malyugin | A61B 17/0231 |
| 2017/0312127 A1 * | 11/2017 | Malyugin | A61B 17/0231 |
| 2018/0303474 A1 * | 10/2018 | Malyugin | A61B 1/32 |
| 2018/0333301 A1 * | 11/2018 | Malyugin | A61F 9/00736 |
| 2020/0305857 A1 * | 10/2020 | Malyugin | A61B 1/32 |
| 2022/0125422 A1 * | 4/2022 | Malyugin | A61F 9/007 |
| 2022/0313237 A1 * | 10/2022 | Cote | A61B 17/0293 |

FOREIGN PATENT DOCUMENTS

| | | |
|---|---|---|
| RU | 14506 U1 | 2/2000 |
| RU | 14505 U1 | 9/2000 |
| RU | 2326630 C1 | 6/2008 |
| WO | WO 95/15120 | 6/1995 |
| WO | WO 00/32141 | 6/2000 |

(56) References Cited

FOREIGN PATENT DOCUMENTS

| WO | 2008/115454 A1 | 9/2008 |
| WO | WO 2008/115455 A1 | 9/2008 |

OTHER PUBLICATIONS

Drawings of U.S. Appl. No. 60/918,405. (Year: 2007).*
Cimberle, M., "New Pupil Expander Easier to Implant, Gentle on the Iris," Ocular Surgery News Europe Asia Edition, [online], May 2006 [retrieved on Mar. 27, 2013]. Retrieved from the Internet URL: http://www.osnsupersite.com/view.aspx?rid=16863.
He et al., "Distribution and Heritability of Iris Thickness and Pupil Size in Chinese: Tire Guangzhou Twin Eye Study", Apr. 2009, IOVS ARVO Journal, vol. 50, Issue 4, pp. 1593-1597.
International Search Report dated Jul. 23, 2008 for International Application No. PCT/US2008/003472, entitled "Ring Used in a Small Pupil Phacoemulsification Procedure".
International Preliminary Report on Patentability dated Sep. 15, 2009 for International Application No. PCT/US2008/003472, entitled "Ring Used in a Small Pupil Phacoemulsification Procedure".
Ma et al., "Technique for removal of a capsular tension ring from the vitreous," Ophthalmology, pp. 1142-1144, 2003.

* cited by examiner

RING USED IN A SMALL PUPIL PHACOEMULSIFICATION PROCEDURE

RELATED APPLICATIONS

This application is a continuation of U.S. application Ser. No. 13/661,982, now U.S. Pat. No. 10,537,470, filed Oct. 26, 2012, which is a continuation of U.S. application Ser. No. 12/074,742, now U.S. Pat. No. 8,323,296, filed Mar. 5, 2008, which claims the benefit of U.S. Provisional Application No. 60/918,405 filed on Mar. 15, 2007. The entire teachings of the above applications are incorporated herein by reference.

BACKGROUND OF THE INVENTION

Field of the Invention

The present invention relates to a ring used in a ophthalmic surgical procedure.

Background Information

There are various ophthalmic procedures that require the dilation of the pupil. For example, cataracteous lenses are typically replaced in a procedure commonly referred to as phacoemulsification or phaco for short. In a phaco procedure the lens is broken up with an instrument, typically with an ultrasonically driven tool. The instrument has an aspiration port that aspirates the broken lens material from the patient's ocular chamber.

It is desirable to extend the pupil during a phaco procedure to provide the surgeon with a wide view of the lens. One technique for extending the pupil includes pulling back the iris with a series of plastic hooks. It is has been found that using plastic hooks can cause damage to iris tissue.

SUMMARY OF THE INVENTION

A ring used to maintain a pupil in an extended position during an ophthalmic procedure. The ring has a plurality of loops.

Described herein is a method of implanting a continuous iris-expanding ring in an eye. The method can include drawing the continuous iris-expanding ring into a cannula, wherein the continuous iris expanding ring transitions from a first expanded configuration into a collapsed configuration in the cannula; inserting a distal end of the cannula into the eye; ejecting the continuous iris-expanding ring from the distal end of the cannula toward an iris of the eye; securing a distal portion of the continuous iris-expanding ring to the iris of the eye; and securing a proximal portion of the continuous iris-expanding ring to the iris of the eye. The iris surrounds a pupil, and the continuous iris-expanding ring is in a second expanded configuration when the proximal portion and the distal portion of the continuous iris-expanding ring are secured to the iris of the eye and extend across the pupil. The continuous iris-expanding ring can be fully expanded into the second expanded configuration from the collapsed configuration after securing the distal portion of the continuous iris-expanding ring to an iris of the eye. The method can further include securing a first lateral portion of the continuous iris expanding ring to the iris of the eye. The method can further include securing a second lateral portion of the continuous iris expanding ring to the iris of the eye. The first lateral portion of the continuous iris-expanding ring can be secured to the iris of the eye after the distal portion of the continuous iris-expanding ring is secured to the iris of the eye. The method can further include retracting a hook through the cannula, wherein the hook is configured to grasp the continuous iris-expanding ring and to draw the continuous iris-expanding ring into the cannula as the hook is retracted through the cannula. A proximal end of the cannula can be connected to an inserter handle and the method can further include sliding a slider on the inserter handle to retract the hook through the cannula. The method can further include moving the proximal portion of the continuous iris expanding ring away from the distal portion of the continuous iris-expanding ring while sliding the slider on the inserter handle. Inserting the distal end of the cannula into the eye can include inserting the distal end of the cannula into an anterior chamber of the eye.

Described herein is a method of implanting a continuous iris-expanding ring in an eye. The method can include ejecting the continuous iris-expanding ring from a distal end of a cannula toward an iris of the eye, wherein the continuous iris-expanding ring is in a collapsed configuration in the cannula prior to being ejected; following ejecting the continuous iris-expanding ring from the distal end of the cannula, securing a distal portion of the continuous iris-expanding ring to the iris of the eye; and securing a proximal portion of the continuous iris-expanding ring to the iris of the eye. The iris surrounds a pupil, and the continuous iris-expanding ring is in an expanded configuration when the proximal portion and the distal portion of the continuous iris-expanding ring are secured to the iris of the eye and extend across the pupil. The method can further include inserting the distal end of the cannula into the eye. Inserting the distal end of the cannula into the eye can include inserting the distal end of the cannula into an anterior chamber of the eye. A distance between the proximal portion and the distal portion of the continuous iris-expanding ring in the collapsed configuration can be different from the distance between the proximal portion and the distal portion of the continuous iris expanding ring in the expanded configuration. The continuous iris-expanding ring can be fully expanded into the expanded configuration from the collapsed configuration after securing the distal portion of the continuous iris-expanding ring to the iris of the eye. The method can further include securing a first lateral portion of the continuous iris expanding ring to the iris of the eye. The method can further include securing a second lateral portion of the continuous iris expanding ring to the iris of the eye. The first lateral portion of the continuous iris-expanding ring can be secured to the iris of the eye after the distal portion of the continuous iris-expanding ring is secured to the iris of the eye. A proximal end of the cannula can be connected to an inserter handle and the method can further include sliding a slider on the inserter handle to retract the hook through the cannula. The method can further include moving the proximal portion of the continuous iris expanding ring away from the distal portion of the continuous iris-expanding ring while sliding the slider on the inserter.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Described is a ring that can maintain a pupil in an extended position during an ophthalmic procedure. The ring has a plurality of loops that capture iris tissue. The ring is configured to extend the pupil when iris tissue is inserted into each loop. An ophthalmic procedure such as phacoemulsification can then be performed on the patient. The ring has a center opening that provides a wide view of the ocular chamber during the procedure.

Figure 1:
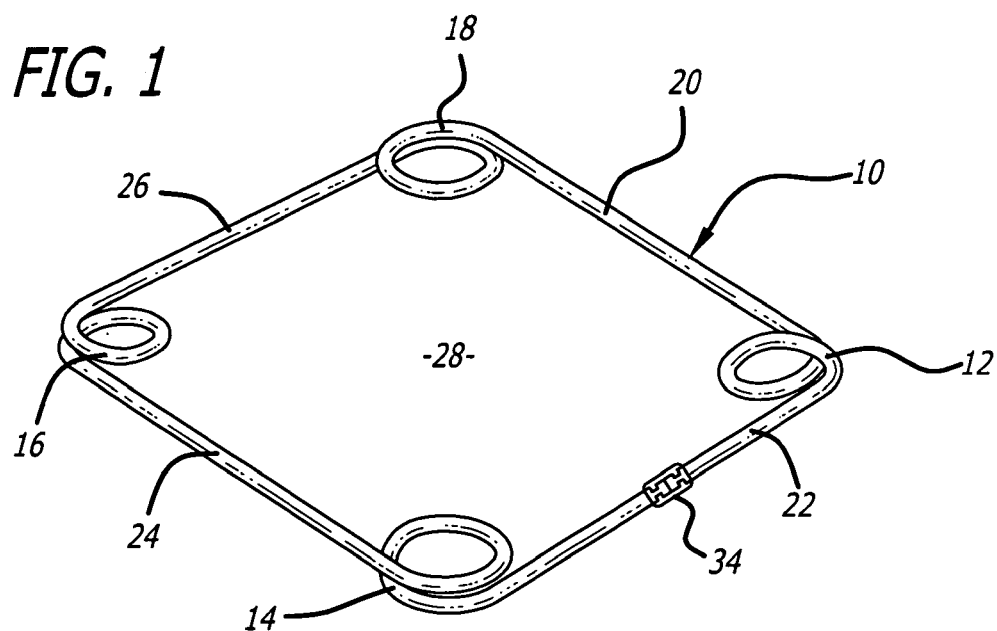
FIG. 1 is an illustration of a ring of the present invention.

Referring to the drawings more particularly by reference numbers, FIG. 1 shows an embodiment of a ring 10 that can be used to extend a pupil during an ophthalmic procedure. The ring 10 has a plurality of loops 12, 14, 16 and 18 located at the corners of four sides 20, 22, 24 and 26. Each loop 12, 14, 16 and 18 may be formed by one full turn. Although one full turn is shown and described, it is to be understood that each loop 12, 14, 16 and 18 may have multiple turns. The four sides 20, 22, 24 and 26 circumscribe a center opening 28.

The ring 10 preferably has a square configuration such that the sides 20, 22, 24 and 26 are of equal dimension. Although a square ring is shown and described, it is to be understood that the ring may have a rectangular configuration where all sides 20, 22, 24 and 26 are not of equal dimension. Additionally, the ring may have a nonrectangular shape. For example, the ring 10 may be shaped as a triangle that has three sides and three loops located at the ring corners. Although three and four sided rings have been described, it is to be understood that the ring may have any number of side and loops. The ring 10 is preferably constructed from a molded plastic material, although it is to be understood that other materials such as metal or plastic coated metal may be employed.

Figure 2:
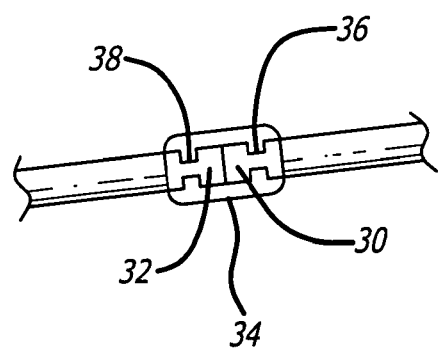
FIG. 2 is an illustration showing an enlarged view of the ring.

FIG. 2 shows a preferred embodiment for constructing the ring 10. One side 20 of the ring 10 has two ends 30 and 32 that are butt attached by an adhesive 34. Each end 30 and 32 may have an indent 36 and 38, respectively. The adhesive 34 can flow into the indents 36 and 38 to increase the strength of the butt attachment of the ring 10. The indents 36 and 38 create surface structure that minimizes shearing and delamination of the adhesive 34 from the ring 10. By way of example, the adhesive 34 may be a biocompatible material such as Class VI epoxy. The adhesive 34 can be applied with a tool (not shown) that insures a repeatable volume and dimensions of the solidified adhesive form.

Figure 3:
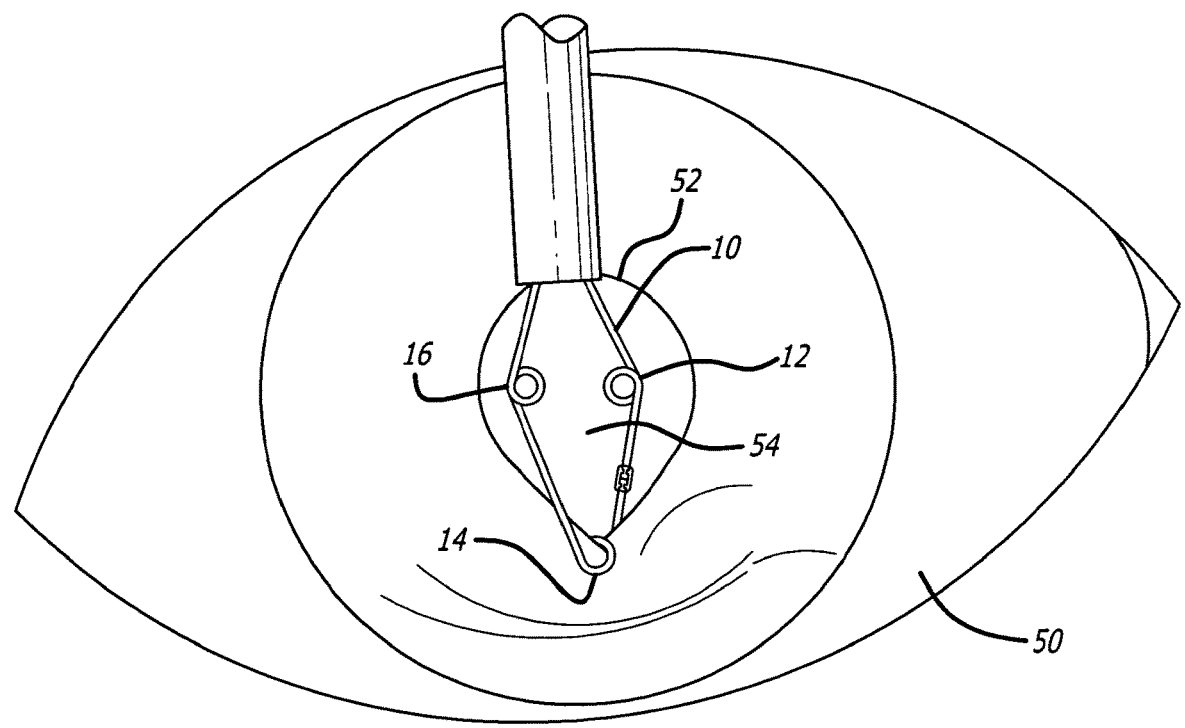
FIG. 3 is an illustration showing iris tissue being inserted into a first loop of the ring.
Figure 4:
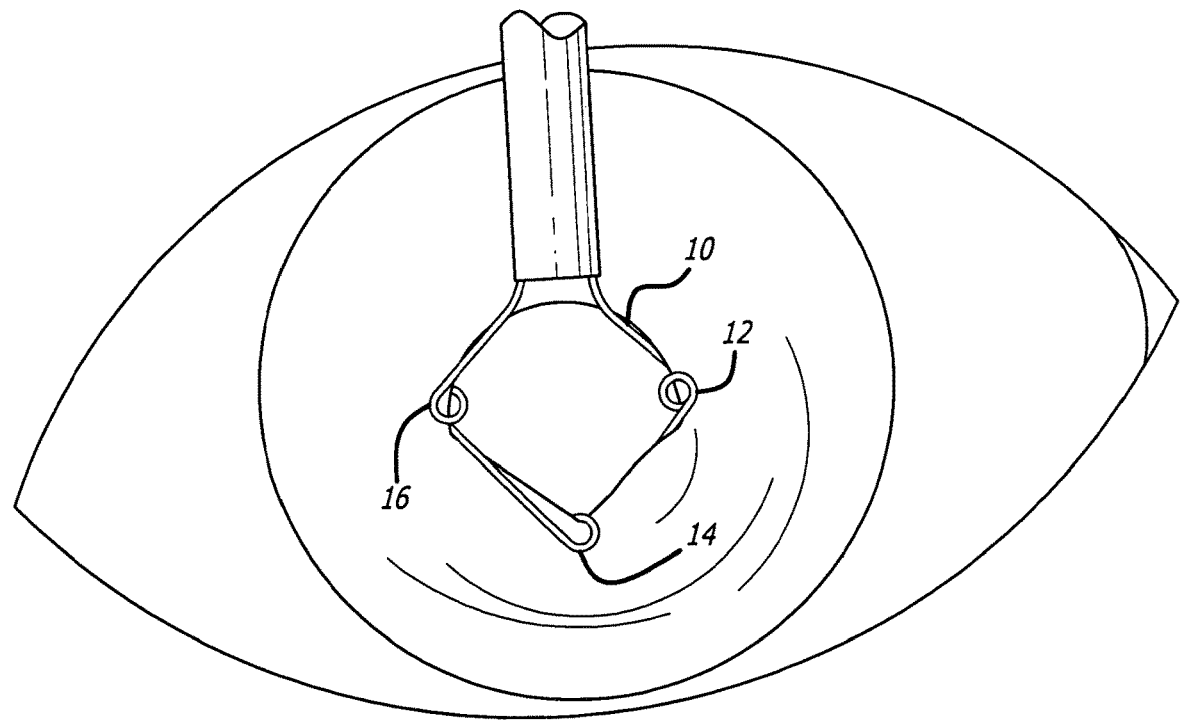
FIG. 4 is an illustration showing iris tissue being inserted into a second loop of the ring.

FIG. 3 shows the initial stages of the ring 10 being inserted into a patient's eye 50 to stretch the iris 52 and extend the pupil 54. A tool such as a forcep (not shown) can be used to pull the iris so that iris tissue is inserted into loop 14 of the ring 10. As shown in FIG. 4, the ring 10 can be manipulated so that iris tissue is inserted into loops 12 and 16.

Figure 5:
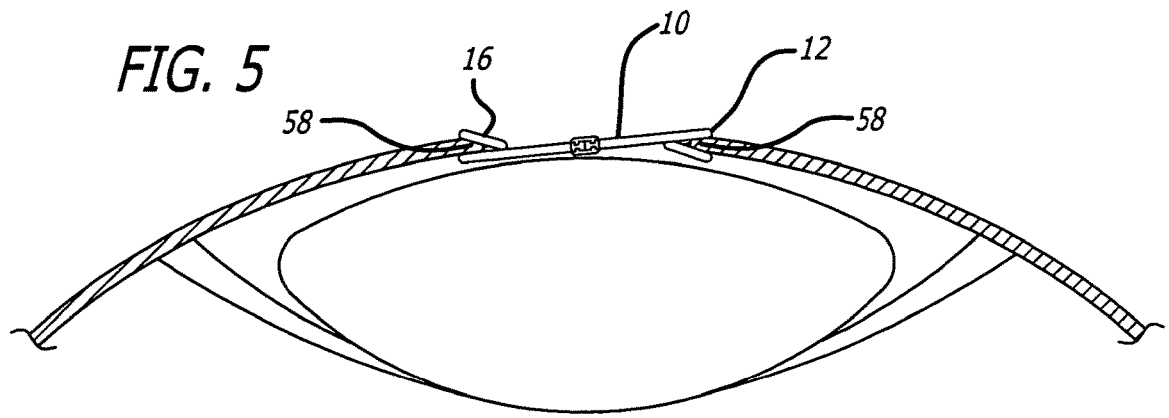
FIG. 5 is an illustration showing the iris tissue within gaps of the loops.

As shown in FIG. 1, an example of the device of the present invention is a polygonal ring formed from a single strand. As shown in FIG. 5 each loop 12, 16, etc. has a gap 58 that receives and captures iris tissue. The gap is wedge-shaped and faces the periphery of the ring 10. It is formed between a top portion of the strand and a bottom portion of the strand. The loop design provides an easy means of inserting and capturing iris tissue. The flexibility of the ring 10 allows the loops to deflect and apply a clamping force onto the iris tissue. The clamping force assist in maintaining the position of the ring relative to the eye.

Figure 6:
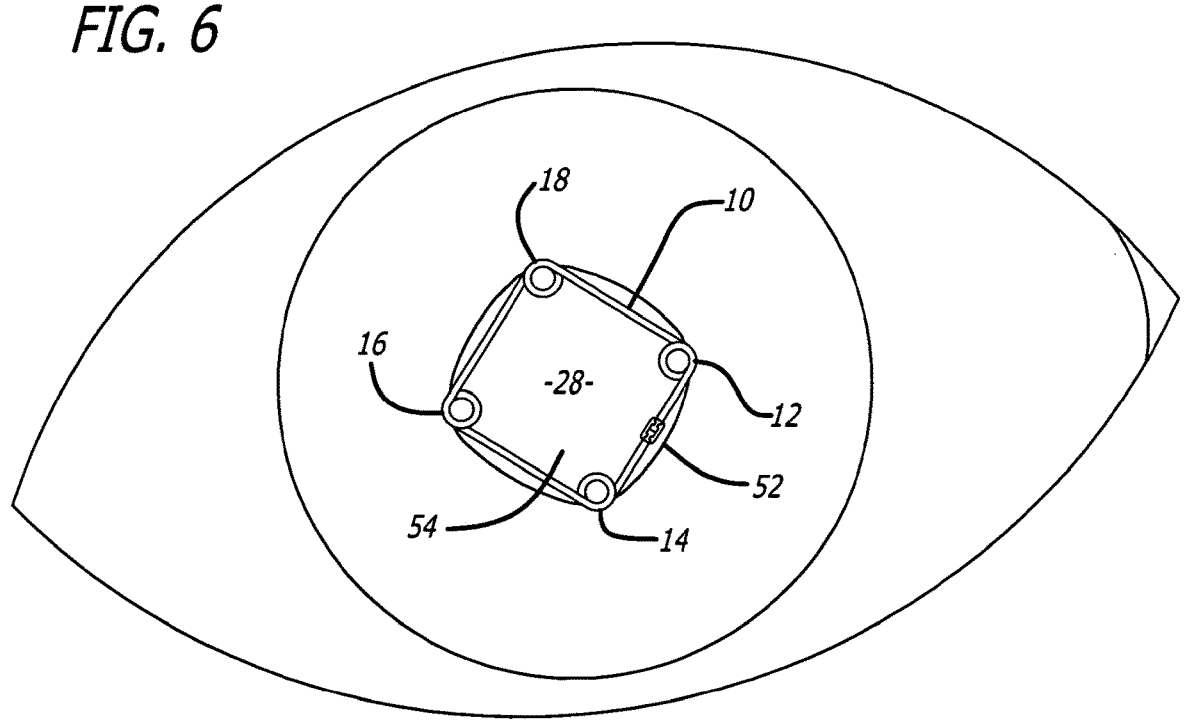
FIG. 6 is an illustration showing a pupil being maintained in an extended position by the ring.

As shown in FIG. 6 iris tissue can be inserted into the second 14 and fourth 18 loops to fully stretch the iris 52 and extend the pupil 54. An ophthalmic procedure can then be performed on the eye. For example, a phaco procedure can be performed wherein the lens is emulsified and aspirated from the eye. The ring 10 maintains the pupil 54 in the fully extended position while the center opening 28 provides a wide viewing area during the procedure. When the procedure is complete one of the sides 20, 22, 24 or 26 can be cut with an instrument and the ring 10 can be removed from the eye.

Figure 7:
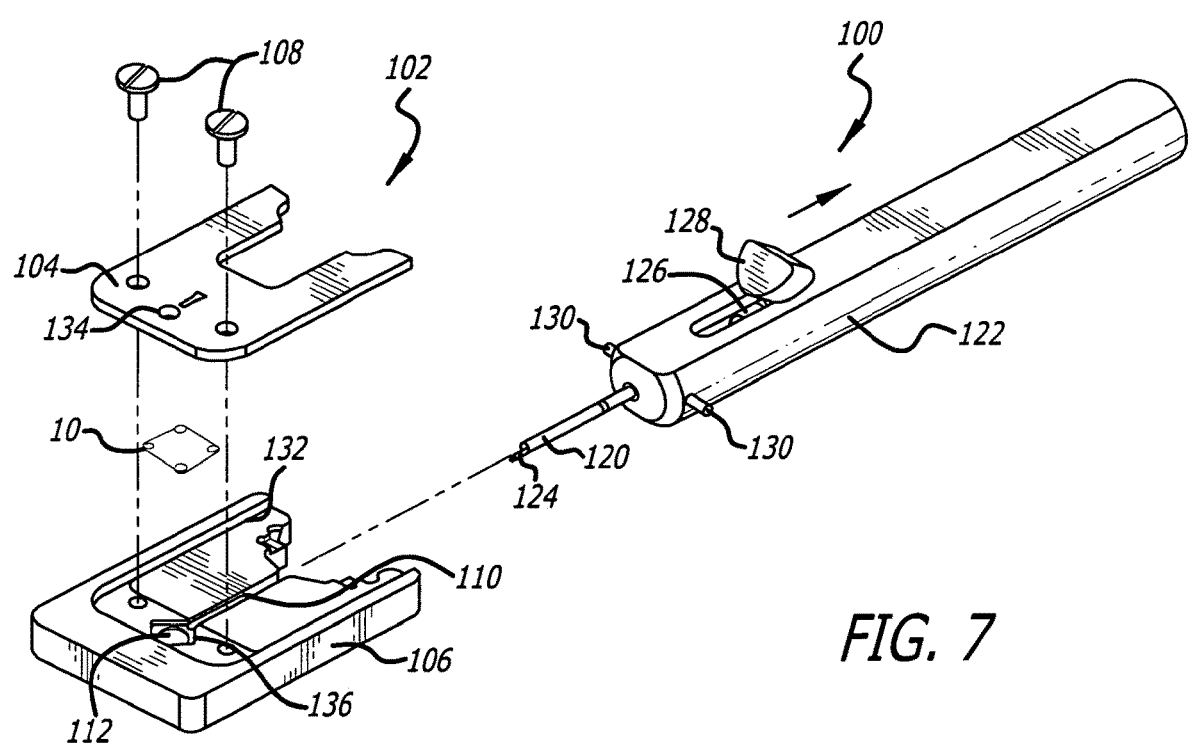
FIG. 7 is a perspective view of an injector and ring plate used to load and inject the ring.

FIG. 7 shows an embodiment of an injector 100 that can be used to inject a ring 10 into a patient's eye. The ring 10 can be loaded into the injector with the use of a ring plate 102. The ring plate 102 may include a cover 104 that is attached to a base plate 106 by fasteners 108. The base plate 106 has a channel 110 and a recess 112. The recess 112 receives the ring 10.

The injector 100 includes a cannula 120 attached to a handle 122. Within the cannula 120 is a wire hook 124. The wire hook 124 is connected to an inner slide tube 126 located within the handle 122. A button 128 is attached to the inner slide tube 126. The injector 100 may also have a pair of guide pins 130 that are attached to the handle 122 and cooperate with corresponding channel features 132 of the base plate 106 to properly align the injector 100 when the cannula 120 is inserted into the base plate channel 110.

In operation, the cannula 120 is inserted into the base plate channel 110. When fully inserted the wire hook 124 extends to approximately the center of the ring 10. The cover 104 may have an opening 134 that allows an operator to visually see the hook 124 within the ring opening. An operator then pulls the button 128 in the direction indicated by the arrow. Pulling the button 128 causes the hook 124 to grasp the ring loops and pull the ring 10 into the cannula 120. The recess 112 has tapered walls 136 to assist in the ring collapsing within the channel 110 for insertion into the cannula 120. Once loaded, the ring 10 can be injected into a patient's eye by pushing the button 128 in the opposite direction.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method of implanting a continuous iris-expanding ring in an eye, the method comprising:

drawing the continuous iris-expanding ring into a cannula, wherein the continuous iris-expanding ring transitions from a first expanded configuration into a collapsed configuration in the cannula;
inserting a distal end of the cannula into the eye;
ejecting the continuous iris-expanding ring from the distal end of the cannula toward an iris of the eye;
securing a distal portion of the continuous iris-expanding ring to the iris of the eye; and
securing a proximal portion of the continuous iris-expanding ring to the iris of the eye;
wherein the iris surrounds a pupil, and the continuous iris-expanding ring is in a second expanded configuration when the proximal portion and the distal portion of the continuous iris-expanding ring are secured to the iris of the eye and positioned opposite each other across the pupil.

2. The method of claim 1, wherein the continuous iris-expanding ring is fully expanded into the second expanded configuration from the collapsed configuration after securing the distal portion of the continuous iris-expanding ring to an iris of the eye.

3. The method of claim 1, further comprising securing a first lateral portion of the continuous iris-expanding ring to the iris of the eye.

4. The method of claim 3, further comprising securing a second lateral portion of the continuous iris-expanding ring to the iris of the eye.

5. The method of claim 3, wherein the first lateral portion of the continuous iris-expanding ring is secured to the iris of the eye after the distal portion of the continuous iris-expanding ring is secured to the iris of the eye.

6. The method of claim 1, further comprising retracting a hook through the cannula, wherein the hook is configured to grasp the continuous iris-expanding ring and to draw the continuous iris-expanding ring into the cannula as the hook is retracted through the cannula.

7. The method of claim 6, wherein a proximal end of the cannula is connected to an inserter handle and the method further comprises sliding a slider on the inserter handle to retract the hook through the cannula.

8. The method of claim 7, further comprising moving the proximal portion of the continuous iris-expanding ring away from the distal portion of the continuous iris-expanding ring while sliding the slider on the inserter handle.

9. The method of claim 1, wherein inserting the distal end of the cannula into the eye comprises inserting the distal end of the cannula into an anterior chamber of the eye.

\* \* \* \* \*